United States Patent
Bichl et al.

(10) Patent No.: US 8,696,780 B2
(45) Date of Patent: Apr. 15, 2014

(54) AIR CLEANER FOR REMOVING AIR POLLUTANTS FROM AN AIR STREAM

(75) Inventors: Christoph Bichl, Gumpoldskirchen (AT); Heinz Winkler, Gumpoldskirchen (AT); Alois Homer, Gumpoldskirchen (AT); Erich Petein, Blumau-Neuriβhof (AT); Maximilian Vojta, Blumau-Neuriβhof (AT)

(73) Assignees: Nonomatic AG, Gumpoldskirchen (AT); Dexwent USA LLC, Atlanta, GA (US)

( * ) Notice: Subject to any disclaimer, the term of this patent is extended or adjusted under 35 U.S.C. 154(b) by 595 days.

(21) Appl. No.: 12/942,615

(22) Filed: Nov. 9, 2010

(65) Prior Publication Data

US 2011/0136567 A1 Jun. 9, 2011

(30) Foreign Application Priority Data

Nov. 12, 2009 (EP) ..................................... 09175857

(51) Int. Cl.
| | |
|---|---|
| *B01D 50/00* | (2006.01) |
| *B01D 39/06* | (2006.01) |
| *B01D 39/14* | (2006.01) |
| *B01D 24/00* | (2006.01) |
| *B01D 59/50* | (2006.01) |
| *F02M 37/22* | (2006.01) |
| *B01D 63/00* | (2006.01) |
| *C02F 1/44* | (2006.01) |
| *B01J 19/00* | (2006.01) |

(52) U.S. Cl.
USPC ................. 55/484; 55/522; 55/523; 210/243; 210/321.88; 210/321.79; 210/321.8; 210/321.78; 422/130

(58) Field of Classification Search
USPC ............... 55/484, 522, 523; 210/243, 321.88, 210/321.79, 321.8, 321.78; 422/130
See application file for complete search history.

(56) References Cited

U.S. PATENT DOCUMENTS

| | | | |
|---|---|---|---|
| 2,286,480 A | 6/1942 | Farr | |
| 3,704,223 A * | 11/1972 | Dietzsch | 204/601 |

(Continued)

FOREIGN PATENT DOCUMENTS

| | | |
|---|---|---|
| DE | 19925439 A1 | 12/2000 |
| EP | 515759 A1 | 12/1992 |

(Continued)

OTHER PUBLICATIONS

International Search Report and Written Opinion completed on May 5, 2011.

*Primary Examiner* — Amber Orlando
(74) *Attorney, Agent, or Firm* — Dilworth & Barrese LLP.

(57) ABSTRACT

The present invention relates to an air cleaner for removing air pollutants from an air stream, for instance such as the cleaning exhaust/intake gas of an amusement machine, said air cleaner comprising a filter device including at least one filter layer (4*a*, 4*b*) held by a filter holder (5) in said airflow substantially perpendicular to a main flow direction thereof and including a plurality of preferably stick-shaped filter elements (6) neighboring each other. In accordance with the present invention, the filter device has no closed surrounding along the circumference of the filter layers, but provides for an open side along at least a portion of the periphery of the filter layer. At least one circumferential side section (7, 8) of the filter layer parallel to or tangential to the longitudinal axis of an outermost filter element is formed as an open side free of flow control elements surrounding the filter layer. Contrary to the prior art where the filter layer is usually enclosed in a tubular flow channel, the present invention avoids such flow-control-elements for guiding the air stream through the filter layer and/or preventing the airflow from diverging away from the filter layer, wherein in particular the filter layer, at its open side, is dispensed with flow-control-elements such as flow guiding surfaces, flow channel walls, fences or housing walls surrounding the filter layer.

19 Claims, 7 Drawing Sheets

(56) References Cited

U.S. PATENT DOCUMENTS

| | | | | |
|---|---|---|---|---|
| 3,993,816 A | * | 11/1976 | Baudet et al. | 428/45 |
| 4,052,315 A | * | 10/1977 | Lindsay et al. | 210/232 |
| 4,268,278 A | * | 5/1981 | Dobo et al. | 419/2 |
| 4,427,424 A | * | 1/1984 | Charpin et al. | 96/8 |
| 4,935,042 A | * | 6/1990 | Sudo et al. | 55/484 |
| 5,069,353 A | * | 12/1991 | Espenan | 220/4.01 |
| 5,104,535 A | * | 4/1992 | Cote et al. | 210/321.8 |
| 5,182,019 A | * | 1/1993 | Cote et al. | 210/321.8 |
| 5,352,361 A | * | 10/1994 | Prasad et al. | 210/321.81 |
| 5,366,625 A | * | 11/1994 | Pedersen et al. | 210/321.78 |
| 5,512,074 A | | 4/1996 | Hanni et al. | |
| 5,554,283 A | * | 9/1996 | Brinda et al. | 210/321.8 |
| 5,584,997 A | * | 12/1996 | Yagihashi et al. | 210/321.79 |
| 5,626,749 A | * | 5/1997 | Lambert et al. | 210/257.1 |
| 5,707,242 A | * | 1/1998 | Mitra et al. | 439/74 |
| 5,743,765 A | * | 4/1998 | Andrews et al. | 439/607.1 |
| 5,993,520 A | * | 11/1999 | Yu | 96/66 |
| 6,183,543 B1 | * | 2/2001 | Buxbuam | 96/11 |
| 6,752,925 B2 | * | 6/2004 | Bolduan | 210/243 |
| 7,686,868 B2 | * | 3/2010 | Rubas | 96/7 |
| 7,708,888 B2 | * | 5/2010 | Mahendran et al. | 210/650 |
| 8,021,619 B2 | * | 9/2011 | Nickel et al. | 422/130 |
| 8,048,306 B2 | * | 11/2011 | Zha et al. | 210/636 |
| 8,075,776 B2 | * | 12/2011 | Mahendran et al. | 210/636 |
| 8,287,743 B2 | * | 10/2012 | Zha et al. | 210/797 |
| 2003/0024107 A1 | * | 2/2003 | Duckett | 29/700 |
| 2004/0069701 A1 | * | 4/2004 | Vasse et al. | 210/321.88 |
| 2004/0076874 A1 | * | 4/2004 | Nickel et al. | 429/104 |
| 2007/0197301 A1 | * | 8/2007 | Cole | 463/46 |
| 2008/0314248 A1 | * | 12/2008 | Peteln | 96/1 |

FOREIGN PATENT DOCUMENTS

| | | |
|---|---|---|
| EP | 1344560 A2 | 9/2003 |
| EP | 1345669 A1 | 9/2003 |
| FR | 629231 A | 11/1927 |
| GB | 28984 A | 0/1911 |
| GB | 823542 A | 11/1959 |
| GB | 1179883 A | 2/1970 |
| WO | 2007/028176 | 3/2007 |

* cited by examiner

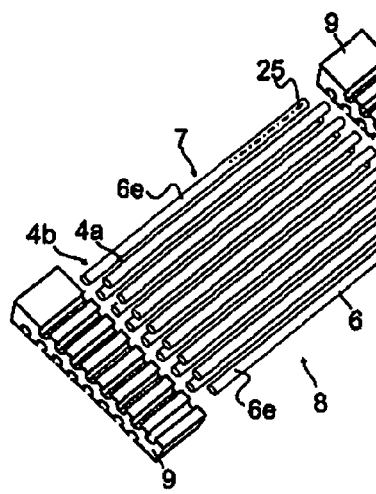
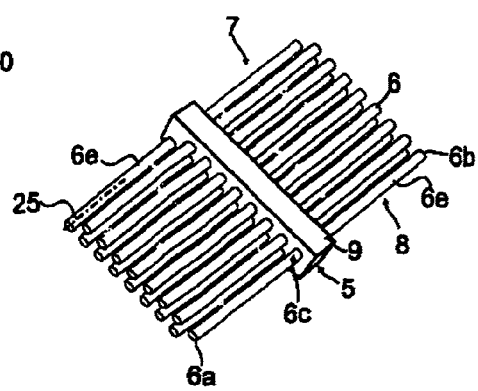
FIG. 8
FIG. 9A
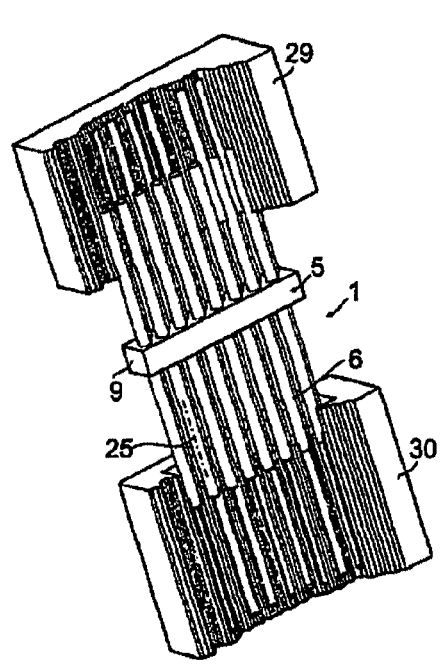
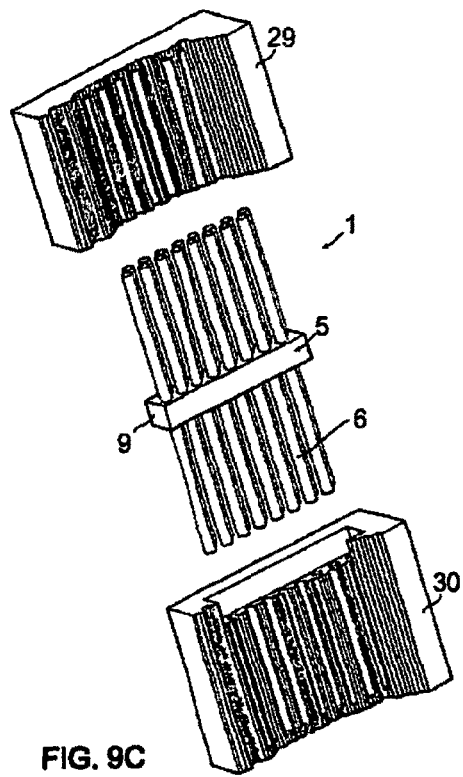
FIG. 9B
FIG. 9C

AIR CLEANER FOR REMOVING AIR POLLUTANTS FROM AN AIR STREAM

BACKGROUND OF THE INVENTION

The present invention relates to an air cleaner for removing air pollutants from an air stream, for instance such as the cleaning exhaust/intake gas of an amusement machine, said air cleaner comprising a filter device including at least one filter layer held by a filter holder in said airflow substantially perpendicular to a main flow direction thereof and including a plurality of preferably stick-shaped filter elements neighboring each other.

An air cleaner of the above mentioned type is known from WO 2007/028176 A1 disclosing a filter device for removing air polluting materials from machine exhaust. The device is provided with a plurality of filter sticks which are held at the opposite ends in a filter housing and arranged in a plurality of layers one above the other with a lateral offset. The said filter sticks are made of a porous material such as plastic foam which is wetted with a fluid such as silicone oil. Such wet filters are very effective in removing air polluting materials including ultrafine particles and gaseous pollutants such as unpleasant odors which are chemically absorbed and neutralized by coming into contact with the fluid. The array of the filter sticks is enclosed in a filter housing forming a tube-like channel in the cross-section of which the filter sticks are placed. This tube-like channel is intended to direct the flow of polluted air through the filter stick array and to prevent the airflow from getting out of the way of the filter sticks. However, such filter stick arrangement is disadvantageous in certain aspects, for example it has shown that there is no uniform filter load on all sticks, in particular the filter load onto the inner sticks is different from the filter load onto the outer sticks. Moreover, such filter stick arrangement is sensible to airflow velocity.

Another filter device having wet filter sticks for cleaning the exhaust air of office machines is known from EP 1 345 669 which suggests to hold the filter sticks in upright position at their opposite ends so that the fluid for wetting the elements is caused to flow downward along the filter sticks by gravity. The said fluid which is oil is stored in a compartment above the filter sticks, wherein an oil pad may be provided in said compartment.

Furthermore, EP 0 515 759 A1 discloses an air filter device provided with a cylindrical housing having its front and back faces covered with grilles so that the air to be cleaned can flow through said housing in which the filter body which may comprise carbon pellets is provided. The said filter housing is arranged at the back side of the motor of a ventilator directing airflow onto the open front face of said filter housing.

GB 28 984 discloses a device for washing smoke with a series of screens being placed in a flue through which the smoke flows. The screens are wetted wherein water coming from a supply tank flows down said screens.

GB 823 542 discloses an apparatus for cleaning combustion gases proceeding from a furnace forming part of a wood waste disposal plant wherein the gas is forced to flow through a channel in which a plurality of tubes is closely spaced from each other to urge the gas to flow through the gaps between the tubes. A scrubbing liquid for the gases flows down the outside of said tubes.

SUMMARY OF THE INVENTION

The present invention aims to improve the aforementioned filter devices and to avoid disadvantages thereof. It is an objective of the present invention to provide an improved air cleaner for removing air pollutants from airflow such as the intake/exhaust air with high efficiency and having a small-sized filter device to allow accommodation thereof in for instance a small interior.

According to the present invention, this objective is achieved by an air cleaner and an amusement machine as described herein. Preferred embodiments of the present invention are explained below in greater detail.

In accordance with the present invention, the filter device has no closed surrounding along the circumference of the filter layers, but provides for an open side along at least a portion of the periphery of the filter layer. At least one circumferential side section of the filter layer parallel to or tangential to the longitudinal axis of an outermost filter element is frameless and formed as an open side free of flow control elements surrounding the filter layer. Contrary to the prior art where the filter layer is usually enclosed in a tubular flow channel, the present invention avoids such flow-control-elements for guiding the air stream through the filter layer and/or preventing the airflow from diverging away from the filter layer, wherein in particular the filter layer, at its open side, is dispensed with flow-control-elements such as flow guiding surfaces, flow channel walls, fences or housing walls surrounding the filter layer. The open side is free of flow restriction means that would prevent transverse diverging of the air and the entire surface of the outermost filter element is exposed to said air stream. At the open side, it is the outermost filter element that directly forms the filter layer's periphery and said outermost filter element extends freely along the periphery (5) of the filter layer. Surprisingly, such an open side enhances the cleaning efficiency of the outermost elements as it is assumed that there are less flow disturbances and the air flows around the outermost filter elements in a more laminar fashion without too high flow speeds so that air pollutants can be absorbed better. As the air flow is not urged through a housing channel of limited cross-section, but also may diverge towards the periphery of the filter layer when flowing through the filter device, the outermost filter elements show better efficiency and there is a more uniform distribution of the filter load onto all filter elements. In addition, the filter device shows a very compact, small-sized structure that allows the air cleaner to be received in small spaces such as the interior of amusement machine cabinets. In accordance with a preferred embodiment of the invention, the filter elements are rigidly connected to each other by said filter holder, wherein the filter elements together with the filter holder form a rigid, self-supporting structure that projects into the air stream from a lateral mounting point positioned at a side of said filter device. Due to the rigid, self-supporting structure of the filter layer, a greater freedom in designing the mounting structure for the filter device is achieved and, on the other hand, the air cleaning efficiency of the outermost section of the filter layer is enhanced due to the frameless filter layer structure.

Preferably, the filter holder does not obstruct more than ½ of the periphery of the filter layer, wherein the filter holder may extend along less than ⅔, preferably less than ½ of the periphery of the filter layer or, according to a preferred embodiment, the filter holder may extend only in a central section of said filter layer leaving the entire periphery free. To achieve such very limited obstruction of the filter layer periphery, the filter holder may be formed by a beam- or stick-shaped holding element that extends transverse to the longitudinal axis of the filter elements. In one preferred embodiment, said beam- or stick-shaped holding element extends parallel to the filter layer plane that is defined by the filter elements so the holding element crosses a plurality of filter elements or filter sections. In another preferred embodiment, the stick-shaped holding element may extend perpendicular to the filter layer plane, wherein preferably the holding element just contacts the centre section of the filter layer which thus extends from said central holding point in a cantilevered fashion towards the periphery of the filter layer which is unsupported.

In order to utilize also the surface of the end sections or tips of the filter elements including the end faces thereof, the filter elements can be supported to have at least one free end. According to a preferred embodiment of the present invention, the filter elements are held in said airflow by a filter holder in a cantilevered fashion with at least one end of the filter elements extending free and unsupported. The absence of any support element at the respective end section of the filter elements avoids any disturbances and allows the end sections to catch air pollutants efficiently.

According to an advantageous embodiment of the invention, the said filter holder is attached to a middle section of the filter elements which thus have two free ends. Such a centered support of the filter elements with a single holding element does not only minimize the holding device's cross-section obstructing the airflow, but also reduces the unsupported length of the filter elements which is approximately only half the length of the entire filter elements.

However, according to another advantageous embodiment of the present invention, the holding device may be attached to an end section of the filter elements so that the said filter elements have only one free, unsupported end. This classic type of cantilevered support facilitates mounting and replacing the filter layers, in particular when there are a plurality of filter layers one of above the other.

Preferably, the holding device includes a substantially bar- or beam-shaped holding element to which all filter elements of a filter layer are rigidly connected. The said holding element preferably extends across the width of the filter layer, wherein the holding element's longitudinal axis may extend traverse, preferably substantially perpendicular to the longitudinal axis of the filter elements. However, according to another embodiment of the invention, the holding element may extend diagonally across the filter elements so that a longitudinal axis of the holding element is angled to the longitudinal axis of the filter elements at an angle of about 30° to 90°, preferably 30° to 60°.

Alternatively to the said cantilevered support structure, the filter elements may be supported at both ends by a pair of holding elements. According to this embodiment, an increased strength against breaking of the filter elements is achieved. The end sections of the filter elements are rigidly connected to respective holding elements so that the respective opposite sides of the filter layer are closed by the said holding elements. Nevertheless, the remaining sections of the circumference of the filter layer, that is the circumferential sides parallel to the longitudinal axis of the filter elements, are open with no holding elements or fences or housing walls surrounding the filter layer.

Generally, there may be different connections between the filter elements and the aforementioned holding element. For example, the holding element may have bore-like recesses corresponding in cross-sectional shape to the filter elements. However, according to a preferred embodiment of the present invention, the said at least one holding element which is preferably bar- or beam-shaped includes a support surface into which the filter elements are embedded with a support section, wherein preferably the support sections of the filter elements are embedded only partly in said support surface so that another part of the circumferential side of the filter element protrudes from said support surface. Due to the unembedded portion (i.e. portion not being embedded) of the support section of the filter elements, the active filter surface is increased and even at their support section the filter elements may absorb air pollutants what provides increased filter efficiency irrespective of the presence of the aforementioned open side of the filter layer. In order to balance the desired increase in the effective filter surface area with the necessary support strength, a sector of $\frac{1}{2}\pi$ to $\frac{3}{2}\pi$ of the circumference of the supported section of the filter elements may be embedded in the support surface of the holding element. Preferably, a sector of $1\pi$ of the circumference is embedded to allow easy removal of both the filter elements and the holding element from a mould.

The said holding element may be formed from a material different from the filter elements material, wherein the support surface of the holding element may have contours adapted to the shape of the circumferential side of the filter elements to be embedded so that the filter elements nestle against said contours. For example, when the filter elements have a cylindrical shape with circular cross-section, the support surface of the holding element may have a groove-shaped depression being cylindrically contoured. In order to connect the filter elements to the holding element, they may be glued into the said embedding contours.

According to another advantageous aspect of the invention, the holding elements may be formed integrally with the filter elements in one part from the same material, wherein preferably a sintering process may be used. In another embodiment of the invention the filter elements and the holding element may be molded, possibly in a foam molding process. For such an integrally one-piece structure of the holding element and the filter elements, the above mentioned cantilevered support structure is preferred since it facilitates removal of the mould halves from the molded filter elements and holding element. In particular, the one-piece structure comprising the holding element and the filter elements may have a shape without undercuts and counterdrafts in the direction of the longitudinal axis of the filter elements and/or a direction perpendicular thereto. In other words, the said one-piece structure comprising the filter elements and the holding element may be shaped such that there is a parting plane preferably extending perpendicular to the longitudinal axis of the filter elements. Preferably, all filter elements of a filter layer are formed in one piece with the holding element(s) for holding the filter layer, wherein even the filter elements of more than one filter layer may be formed in one piece with the holding element thereof.

Basically different materials may be used for the filter elements and optionally for the holding element, wherein in accordance with a preferred embodiment the filter device is a wet filter device including a suitable fluid for wetting the structural material of the filter elements. In other words, the filter elements may be designed as storage medium for a chemically and/or physically active fluid, which adsorbs or absorbs air-polluting materials. Preferably, fluids such as oils, emulsions or liquids may be used depending on and adjusted to the type of pollutants which are present in the air to be cleaned. Optionally, antibacterial, antiviral, antimycotic or fungicidal agents may be added to the wetting fluid. The base material of the filter element which is wetted may comprise different, preferably porous materials such as plastic foams, organic, inorganic or natural fibres such as cellulose or polyester, wherein it is a preferred embodiment to use filter elements made from PU foam wetted with silicone oil.

Depending on the application and the type of pollutants to be filtered, it is however possible, to use other filter materials which may be wetted or not wetted, wherein it may be sufficient for some applications, to use porous particle filter materials such as fabrics, sponge rubber, foamy expanded plastics or other cellular material for collecting the particles coming with the air passing through the filter.

In order to be able to easily adapt the filter to different operating conditions and vary the filter device in size and effective filter surface, the filter device is given a modular structure consisting of basic components which can be attached to each other in varying numbers and/or varying orientations. In accordance with a preferred embodiment of the invention, the holding device for holding the filter elements is designed such that it can be connected with a holding device having the identical shape. In particular, the holding device is provided with hermaphrodite connecting means for connecting at least two filter holders to each other to create at least two filter layers one above the other. Consequently, a stack of filter layers can be created just by connecting the desired number of holding devices each holding a filter layer including a plurality of filter elements.

In order to avoid an arrangement of the filter elements in different filter layers one behind the other, it is preferred to have the filter elements positioned offset to the aforementioned hermaphrodite connecting means in a way that—when two filter holders are connected to each other—the filter elements in a first filter layer overlap the spacings between the filter elements in a second layer when viewed in the direction of the airflow.

In accordance with a particularly advantageous embodiment, the aforementioned holding element of the holding device is provided with the said hermaphrodite connecting means on a back side opposite to the support surface where the filter elements are embedded. Consequently, two beam-shaped holding elements can be connected to each other with their back sides facing each other.

The filter elements basically may have different geometries and shapes, wherein it is preferred to have generally elongated, more preferably stick-shaped filter elements with a length to diameter ratio of more than 5, in particular more than 10, that means the stick-shaped filter elements may have a length at least five times the diameter of the filter element. The cross-sectional shape also may vary and may be adapted to operating conditions. For example, the filter elements may have a triangle or a polygonal cross-section, wherein in particular a rectangular or oblong cross-section may be provided. However, in accordance with a preferred embodiment of the invention, the filter elements advantageously have a rounded cross-section, for example a circular, oval or elliptical cross-section to achieve a smooth flow around the filter elements to enhance the absorption of pollutants. The cross-sectional shape may vary along the longitudinal extension of the elongated elements, for example in terms of a diameter varying along the length or a triangle shape becoming a rounded cross-section. However, according to a preferred embodiment, the filter elements have an elongated shape with a substantially continuous, preferably constant cross-section.

In accordance with a preferred embodiment of the invention, the filter elements are substantially straight rods which are arranged substantially parallel to each other in a filter layer. If the filter device contains a plurality of filter layers, the filter rods in different layers may be arranged parallel to each other with the filter rods in different layers being offset to each other such that the filter rods in a first layer overlap the spacings between the filter rods in a second layer when viewed in the direction of airflow.

According to a further preferred embodiment of the present invention, the filter elements of at least one filter layer may be formed by at least one curved, snake-shaped and/or preferably spiral filter rod having sections parallel to and spaced apart from each other. In other words, there may be only one continuous, rod-shaped filter body, the sections of which form the plurality of filter elements mentioned at the beginning. For example, the snake-like filter rod may meander or correspond to a Greek key pattern having substantially straight legs parallel to each other and neighboring each other. In accordance with a preferred embodiment of the invention, however, the snake-like filter rod has a spiral shape, for example the shape of a logarithmic spiral or the shape of a linear spiral. Filter layers including such spiral filter rods provide for a large effective filter surface in comparison to a small surface of the holding device, wherein the large effective filter surface can be achieved despite a rather compact structure and small circumference of the filter layer.

Preferably, such a spiral-shaped filter rod is supported in a cantilevered fashion as mentioned before, wherein advantageously the inner end of the spiral filter rod is attached to a holding element of the holding device.

In order to enhance affectivity of the filter, a plurality of spiral filter rods may be combined with each other, wherein it is preferred to have a first spiral filter rod rotationally offset relative to a second spiral filter rod. In particular, the rotational offset of the plurality of spiral filter rods is chosen such that a first spiral filter rod overlaps the spacings between the legs of a second spiral filter rod when viewed in the direction of the spiral axis, wherein preferably the said plurality of spiral filter rods have a common spiral axis.

In order to provide for a compact, small-sized support structure, the said plurality of spiral filter rods can be connected with their inner ends to a common holding element preferably having a cylindrical-shape and extending substantially parallel to the spiral axis. Depending on the geometry and shape of the filter rods, two spiral filter rods may be arranged in one common plane or, in the alternative, in two substantially parallel planes spaced apart from each other. The later arrangement in parallel planes spaced from each other is preferred in terms of a better interlace pattern or overlap which helps to avoid that the airflow passes the filter layers without contacting the filter elements. The air passing through a gap between two filter elements of the first layer straight forwardly flows against a filter element of the second filter layer.

In order to allow easy manufacturing, the spiral filter elements may have shapes identical to each other.

In the alternative, at least two spiral filter elements may have shapes complementary to each other such that a first spiral filter element exactly fits in the spacing between the legs of the second spiral filter element. Such complementary shape allows cutting the filter elements out of a common preferably plate-shaped blank.

The filter layer(s) of the filter device may be mounted to a basic support structure directly by means of the aforementioned holding elements. For example, the filter layer may be mounted to ventilating means for urging the airflow through the filter device, wherein for example the holding element may be attached to the driving unit for driving the ventilator blades or a driving unit support. According to a preferred embodiment of the present invention, the filter device can be mounted directly onto a preferably channel-shaped ventilation housing surrounding the driving unit and/or the ventilator blades of the ventilating means and forming a channel for the airflow to be directed onto the filter device, wherein preferably said filter device is positioned in front of an opening orifice of the ventilation housing in the air stream exiting therefrom. However, alternatively to such direct mounting it is also possible to provide for an indirect mounting of the filter layer. The provision of mounting means connecting the filter device to the ventilating means and holding the filter device at the ventilating means in a defined positional relation thereto achieves a very compact, small-sized air cleaner that may be mounted within a very limited space such as the housing of a gaming apparatus. The filter device basically may be positioned on either side of the ventilating means.

According to an advantageous aspect of the invention, the filter device is held by the filter holder at a side of the driving unit of the ventilating means opposite to the ventilator blades so that the motor or drive unit of the ventilating means is positioned between the ventilator blades and the filter device, or at the side of the ventilator blades that is opposite to the driving unit so that the ventilator blades are positioned between the filter device and the driving unit, wherein in either case a coaxial arrangement is preferred where the centre axis of the ventilator blades, the drive unit and the filter device are substantially coaxially arranged. It is also within the scope of the present invention to arrange a filter layer on each side of the ventilating means, that is one filter device at a side of the driving unit of the ventilating means opposite to the ventilator blades, and another filter device at the side of the ventilator blades that is opposite to the driving unit. Such mounting of the filter device at one of the end faces of the ventilating means does not only provide for a compact, small-sized arrangement, but also achieves high efficiency in separating the air-polluting materials since the air stream is precisely directed through the filter layer(s). Said filter layer(s) may have the aforementioned design including a plurality of stick-shaped filter elements or the at least one curved, snake-shaped or spiral filter rod, but the filter layer also may be formed by a continuous sheet-like porous element made of, for example, a spongy foamed or cellular material, wherein it is possible to combine more than one such sheet-like layer in a multi-layer arrangement. Nevertheless, according to a preferred embodiment, one of the aforementioned filter layer designs including elongated filter elements neighboring each other with a gap therebetween, is used for the filter device.

In particular when the filter device is held by the filter holder at the ventilating means, it is preferred to have a driving unit support that comprises a preferably L-shaped support element that includes a first leg connected to the ventilating means and a second leg having mounting means for mounting the device to any external structural element such as the housing of a gaming machine, a support strut etc. The said two legs are preferably connected to each other in a rigid manner, more preferably they are integral with each other made from a sufficiently rigid material such as metal or plastics. More preferably, the first leg extends substantially perpendicular to the axis of rotation of the ventilating blades, wherein the said first leg may include a central recess that is at least as large as the circular area defined by the rotating ventilator blades and thus giving clearance for the air stream of said ventilator blades.

The second leg of said support element preferably extends substantially parallel to the air stream along a lateral side of the driving unit at a distance spaced apart from said driving unit.

Such angled support element allows for mounting the air cleaner in very little space and forms a very compact mounting structure that is easy to manufacture, but nevertheless rigid and sufficiently stiff.

Preferably said first leg of the support element together with said filter device is mounted to the opening orifice of a channel shaped ventilation housing surrounding the driving unit and/or said ventilator blades.

According to another advantageous aspect of the present invention, the filter layer of the filter device are inserted in a mounting frame surrounding the filter layer at a circumference thereof, said mounting frame including an insertion recess fully overlapping the projected area of the filter layer when viewed in the direction of the airflow, thus enabling insertion and removal of the filter layer into/from the mounting frame in the direction of the airflow. Contrary to the prior art, such mounting structure significantly facilitates mounting, demounting and replacement of the filter layer, since it is not necessary to thread the filter elements separately into holding recesses as it is the case in the prior art where the filter elements are to be inserted in a direction perpendicular to the airflow and/or parallel to the longitudinal direction of the filter sticks. This is advantageous in particular when the filter elements are supported in a cantilevered fashion so they have free, unsupported ends.

The insertion recess of the said mounting may have a window opening shape basically corresponding to the shape or circumference of the filter layer to be inserted. Preferably, the insertion recess is defined by a cylindrical through hole through the mounting frame, wherein the inner circumference of the through hole basically corresponds to the outer circumference of the filter layer such that the filter layer is hold in said insertion recess by means of a press fit. The insertion recess does not necessarily hold each side or the entire circumference of the filter layer, but may hold the filter at opposite sides only. If the filter layer consists of an array of parallel, substantially straight filter sticks, it is preferred to have the press fit to the insertion recess at the ends of the said stick-shaped elements, whereas the other two sides of the filter layer parallel to the longitudinal axis of the filter sticks may have some spacing to the surrounding insertion recess. Press fitting the ends of the filter sticks into the insertion recess and/or the holding elements provided at these ends of the filter sticks into the insertion recess, uses the filter sticks as compression bars or columns which are subjected to buckling strain only.

The air cleaner is preferably provided inside the cabinet of a for instance gambling or amusement machine so that the air is filtered inside the housing of the machine.

Amusement machines such as coin operated gambling machines are usually operated in casinos or gambling halls where the air is often polluted due to smoking, human transpiration or the smell of food. Another issue are the exhaust gases created by the amusement machines which are usually provided with electronic controllers and displays producing hot exhaust air often polluted with dust or other particles. Therefore, it would be desirable to clean the air in the rooms where such amusement machines are used, wherein it would be desirable to have the intake air of the machines cleaned to avoid harm to the sensitive components of the amusement machines and, on the other hand, to clean the exhaust gases of such amusement machines to achieve a better air condition in the room where the machines are operated to improve the sense of comfort of the players using the amusement machines.

Consequently, the air cleaner cleans both the intake air and the exhaust air of the amusement machine, thereby improving the quality of the air in the respective room of the casino or gambling hall and thus improving the sense of comfort of the visitors, and on the other hand, protects the electronic components of the amusement machine against the position of pollution particles present in the intake air. Although the air cleaner is preferably used in an amusement machine, there are further options for using the air cleaner. For example, the air cleaner can be used for other office machines such as laser printers, for household appliances such as vacuum cleaners. Other advantageous fields of use are vehicles, in particular automobiles where the air cleaner may be used to clean the air inside the passenger's cabinet, or in the field of air conditioning and heating systems, vacuum cleaners or various other kind of household products that may apply air filters, military equipment, airplane industry, steel and heavy metal industry, etc. Another advantageous field of use is manufacturing pharmaceuticals or in the medical industry.

BRIEF DESCRIPTION OF THE DRAWINGS

In the following, preferred embodiments of the present invention are described in greater detail with reference to the accompanying drawings. In said drawings it is shown in:

FIG. 8: an exploded view of two layers of straight filter rods which are held by two holding elements at their ends, wherein said holding elements are provided with support surfaces on opposite sides thereof into which the filter elements are embedded, FIG. 9: a perspective view of a plurality of straight filter rods arranged in two layers one above the other and held by a holding element attached to middle sections of the said stick-shaped filter elements which thus have two free unsupported ends.

DESCRIPTION OF THE PREFERRED EMBODIMENTS

Figure 1:
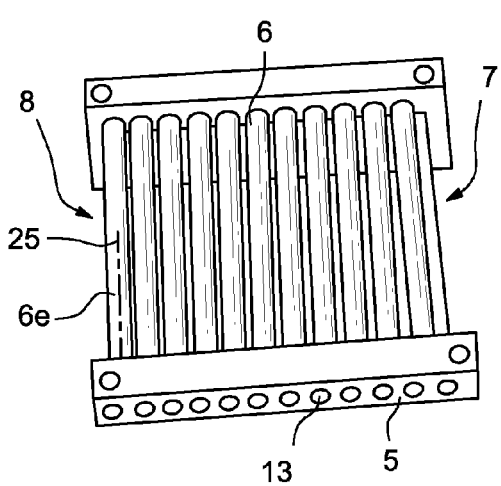
FIG. 1: a perspective view of a filter device according to a preferred embodiment of the invention, wherein stick-shaped filter elements are arranged in parallel with each other and held by a holding device at opposite ends.
Figure 2:
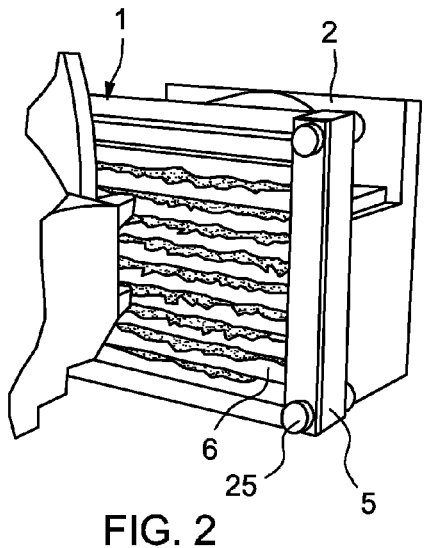
FIG. 2: a perspective view of the filter device of FIG. 1, wherein the filter device is mounted to a ventilator urging an airflow through the filter layer, wherein the filter elements are shown in a used state showing the pollution of the filter elements.

FIG. 1 shows a filter device 1 comprising a plurality of filter elements 6 which are formed by straight filter rods 13 in this embodiment. The said filter elements 6 are arranged in a first filter layer 4a and a second filter layer 4b one above the other, wherein the filter elements 6 basically extend parallel to each other. As can be seen from FIG. 1, FIG. 6 and FIG. 7, the filter elements in different layers are preferably offset relative to each other so that the filter elements 6 in a first layer 4a overlap with spacings between the filter elements 6 in the second layer 4b. In particular, both filter layers 4a and 4b may have the same partition between the filter elements, wherein the offset perpendicular to the longitudinal axis of the filter elements corresponds to half the distance between two neighboring filter elements, cf. FIGS. 6 and 7.

Figure 7:
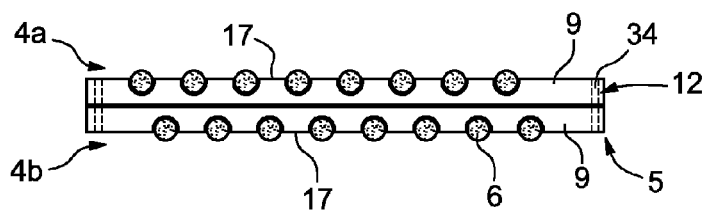
FIG. 7: a front view of two holding elements connected to each other similar to FIG. 6, wherein the connecting means include through holes in both holding elements which can be locked to each other by means of inserting connection pins into said through holes.
Figure 10:
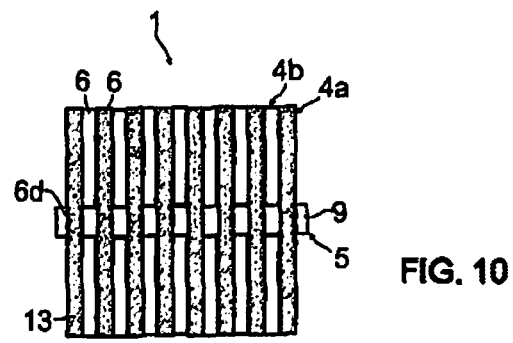
FIG. 10: a front view of the filter device of FIG. 9 in the direction of the airflow through the filter device.
Figure 11:
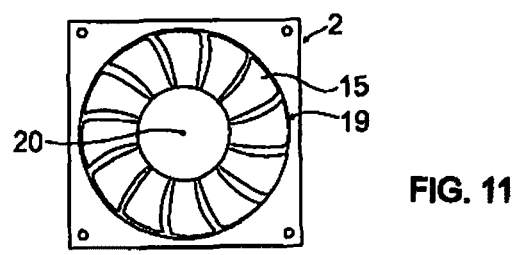
FIG. 11: a front view of a ventilating means for urging airflow through the filter device.
Figure 12:
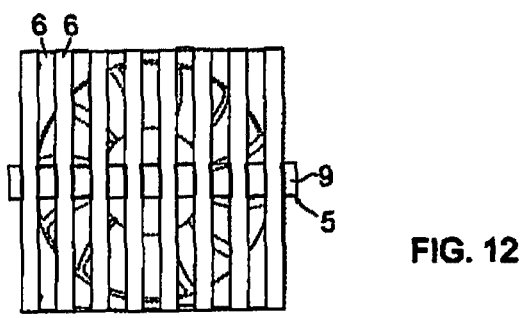
FIG. 12: a front view of the filter device of FIG. 10 attached to the ventilating means of FIG. 11, FIG. 13: a side view of the filter device attached to the ventilating means of FIG. 12, wherein the two holding elements for holding the filter elements are held together and connected to the ventilating means by means of lateral, cramp-like fastening clamps engaging with locking projections on the ventilating means.

Although the filter elements and the partitioning may have different dimensions, the spacings between neighboring filter elements 6 in one layer 4 has a width preferably and approximately corresponding to the diameter of a filter element 6, cf. FIG. 7. Consequently, if the two layers 4a and 4b would be positioned in one common plane, the filter elements 6 would touch each other and form a closed panel. However, the diameters and/or the partition between the filter elements may vary and thus other geometrical structures are possible.

Figure 6:
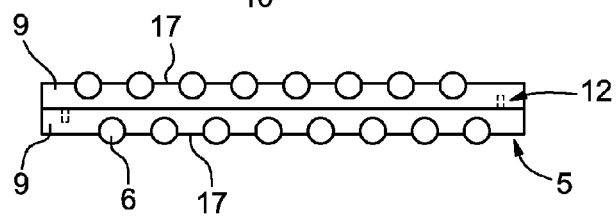
FIG. 6: a front view of the two holding elements of FIG. 5 after having been connected with each other.

As shown by FIGS. 6 and 7, the distance between the filter elements 6 in the different filter layers 4a and 4b also may be in the range of the diameter of the filter rods, wherein it is an advantageous embodiment that the distance between the upper side of the first layer to the lower side of the upper layer, when measured in the direction of airflow, is slightly smaller than the diameter of the filter elements. Although different filter elements may have different diameters, it is preferred to have the same diameter for all filter elements. As shown in the figures, the filter elements can have a cylindrical shape with circular cross-section.

In accordance with a preferred embodiment, the filter elements 6 of a filter layer 4a are held in position by a filter holder 5 comprising at least one holding element 9 which is preferably bar- or beam-shaped as shown in the figures. More particularly, a holding element 9 may be used which has a support surface 10 into which the filter elements 6 are embedded with the circumferential sides of their support section 6d.

Figure 3A:
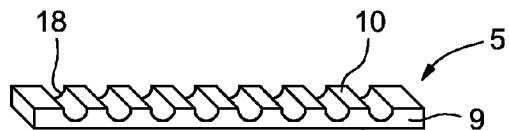
FIG. 3: a preferred embodiment of a holding element of the holding device for holding the filter elements, wherein part a of FIG. 3 shows a perspective view of the beam-shaped holding element as such, that means without filter elements attached thereto so that the groove-shaped support surface of the holding element can be seen, and part b of FIG. 3 shows a front view of the holding element with filter elements embedded in the support surface of the holding element.
Figure 3B:
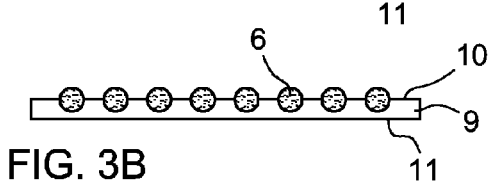

As shown in FIG. 3, the support surface 10 of the holding element 9 may have contours adapted to the circumferential contour of the filter elements 6. In particular, the said support surface may have groove-shaped depressions in which the support sections 6d of the filter elements 6 are nestled or embedded so that there is a two-dimensional contact between the filter elements 6 and the holding element 9. When cylindrical filter rods are used, the said depressions in the support surface 10 of the holding element 9 may be formed as cylindrical support grooves 18.

As can be seen from FIG. 3, the filter elements 6 are embedded in the support surface 10 of the holding element 9 only in part so that a partial sector of the circumferential surface of the filter elements 6 is embedded in the holding element 6, whereas the remaining sector of the circumferential surface of the filter elements is not embedded and/or may protrude above the said support surface 10. In the embodiments shown in the figures, the filter elements 6 are embedded in the holding element 9 with half of their diameters. In other words, a sector of ½π is embedded, cf. FIG. 3.

Figure 5:
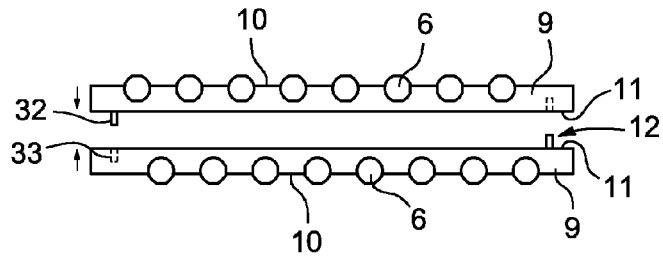
FIG. 5: a front view of two holding elements with filter elements attached thereto in a back side to backside position ready for connecting the two holding elements, wherein hermaphrodite connecting means are shown.

The back surface of the holding element 9 opposite to the embedded filter elements 6 forms a substantially flat mounting surface 11 which allows two holding elements 9 to be connected with each other back side to back side as it is shown in FIGS. 5-7. Thus, a modular filter device 6 is created, wherein multiple filter layer 4 can be positioned one above the other in an easy way.

As shown by FIGS. 5 and 6, the holding element 9 may be provided with hermaphrodite connecting means 12 which allow identically shaped holding elements 9 to be connected with each other. In the embodiment of FIGS. 5 and 6, the said hermaphrodite connecting means 12 include a connecting pill 32 and a connecting hole 33 positioned at opposite sides of the said support surface 10, wherein the connecting pin 32 and connecting hole 33 are spaced the same distance from the centre of the holding element 9 so that the holding elements 9 can be mounted atop of each other in a congruent fashion.

As can be seen from FIGS. 5 and 6, the filter elements 6 are offset with respect to the centre of the holding element 9 and/or the centre between the connecting means 12, wherein the offset is perpendicular to the longitudinal axis of the filter elements 6. In particular, the said offset is such that the filter elements 6 of one layer 4a overlaps with the spacings 17 between the filter elements 6 of the other filter layer 4b, when the two holding elements 9 are connected to each other as shown in FIG. 6.

Figure 4:
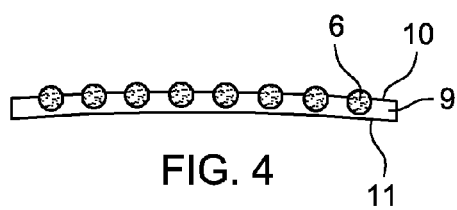
FIG. 4: a front view of a holding element with filter sticks attached thereto similar to FIG. 3, wherein the embodiment of FIG. 4 shows a slightly bended, still beam-shaped holding element being elastic and having a slightly concave back surface in its unbended condition.

In order to strengthen the frictional locking of two holding elements 9, the latter may be made of an elastic material and/or may have a slight bending as shown in FIG. 4 so that it is made subject to elastic deformation when connected to another holding element 9.

Alternatively to the connecting pins 32 and connecting holes 33 shown in FIGS. 5 and 6, other connecting means 12 may be provided. For example, the holding elements 9 may be provided with through holes 34 into which connection pins or screws or other engagement means may be inserted as it is shown in FIG. 7. Preferably, the said through holes 34 are positioned such that the through holes 34 in different holding elements 9 are aligned with each other when the said different holding elements 9 are put on to each other back side to back side in a congruent fashion.

As shown in FIG. 8, two holding elements may be attached to the opposite end sections 6a and 6b of the filter elements 6 so that both ends of the filter elements 6 are supported and held in position.

In an alternative embodiment shown in FIG. 9, the filter elements 6 are supported in a cantilevered fashion so that the filter elements 6 have free, unsupported ends 6a and 6b. As shown in FIG. 9A, a single holding element 9 may be attached to the middle section 6c of the filter elements 6 so that the said filter elements 6 have two unsupported free ends 6a and 6b. Such a cantilevered support of the filter elements 6 does not only reduce the size of the filter holder 5 and thus increases the effective filter surface of the filter elements 6, but also facilitates the production of filter element 6 and the holding element 9 in a molding process. In particular, such support structure as shown in FIG. 9 facilitates the demolding step and removing the mould halves from the filter elements 6 and the holding element 9 even when the filter elements 6 and the holding element 9 are formed integrally with each other in one piece. As can be seen from FIG. 9, a one-piece structure comprising the holding element 9 and the filter element 6 may have a shape without undercuts and counterdrafts in the direction of the longitudinal axis of the filter elements so that there is a parting plane perpendicular to the longitudinal axis of the filter sticks.

As can be seen from FIGS. 9b and 9c, the molding halves 29 and 30 used for molding/sintering the filter elements 6 and the holding element 9 in one piece may be removed by moving the said halves 29 and 30 away from each other in a direction substantially parallel to the longitudinal axis 25 of the filter elements 6.

In order to maximize the effective filter surface, the holding element 9 may be made of the same material as the filter sticks which further facilitates the molding process. However, even if the said integral one-piece structure is provided, the holding element 9 and the filter element 6 may be made of different materials, for example by means of a two-component molding process. This allows the holding element 9 to be made of a more rigid material and/or a strengthened material.

FIGS. 10-13 show an embodiment where a plurality of straight filter rods 13 are supported by a common holding bar at a middle section 6c similar to the embodiment of FIG. 9. Contrary to the embodiment of FIG. 9, the filter elements 6 are embedded in the support surface 10 of two holding elements 9 which are connected to each other back side to back side as explained with reference to FIG. 7. As can be seen from FIG. 13, two layers 4a and 4b of filter elements 6 are held by two holding elements 9 lying on to each other with their back sides.

In order to blow the air to be cleaned through the filter device 1, a ventilating means 2 can be provided, said ventilating means 2 comprising a ventilating wheel 19 which is rotatable about a ventilator axis 20 and includes a plurality of ventilator blades 15 connected to said ventilator axis 20. Furthermore, the ventilating means 20 includes a driving unit 16 which typically may comprise an electric motor received within a housing 21 which is supported by a driving unit holder.

Figure 13:
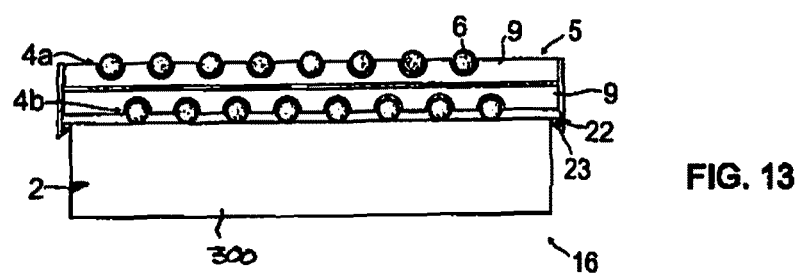
Figure 18:
FIG. 18: a side view of the filter device of FIG. 17 attached to the back side of the driving unit of a ventilating means or a holding frame for holding such driving unit.
Figure 18:
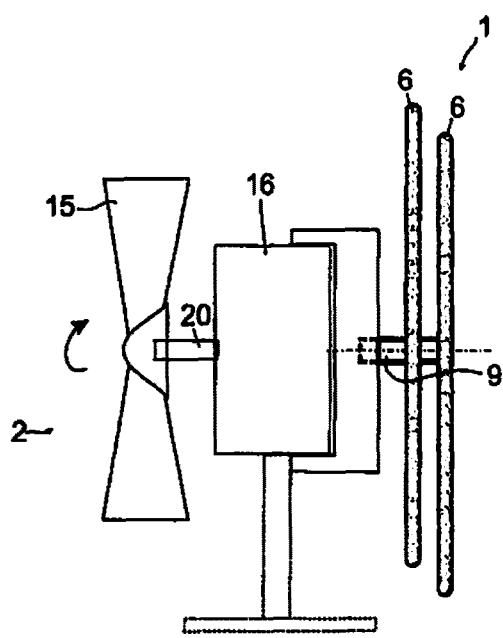
Figure 23:
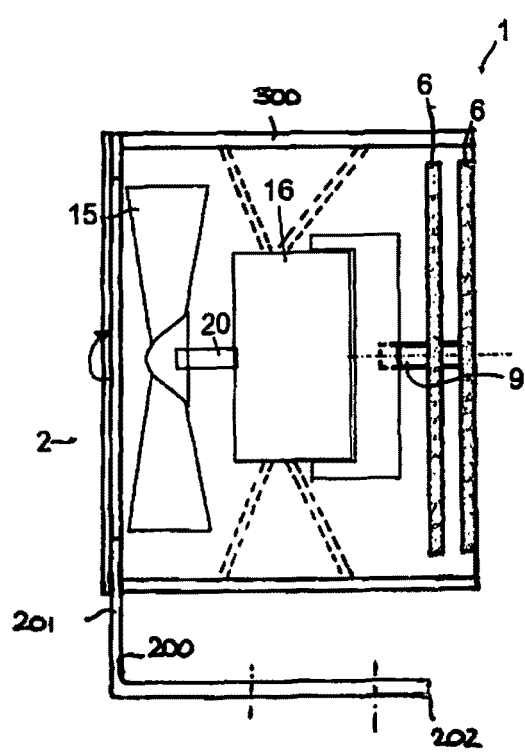
FIG. 23: a side view similar to FIG. 18 showing a support structure including an L-shaped support element for supporting the ventilating means to which the filter device is attached, in accordance with another preferred embodiment of the invention.

As shown by FIG. 13, the filter device 1 is positioned in front of the ventilating means 2 with the filter layers 4 being substantially perpendicular to the ventilator axis 20 and/or perpendicular to the main direction of airflow created by the ventilator blades 15. More preferably, the filter device 1 is positioned in front of the opening orifice of a preferably tube- or channel-shaped ventilation housing 300 surrounding or enclosing the driving unit and the ventilator blades of said ventilating means 2, wherein the filter device may be directly mounted to the ventilating housing 300. In the embodiment of FIG. 13, the filter device 1 is positioned in front of the ventilating wheel 19, however, alternatively or in addition it also could be positioned at the back side of the driving unit 16 opposite to the ventilating wheel 19 as it is shown in FIG. 18 and FIG. 23. By such (an) arrangement(s), the filter device 1 may substitute any protective grating that may be necessary as protection against undesired touching or contacting ventilator blades 15 in particular in a rotating state.

Preferably, the filter holder 9, more particularly the holding elements 9 thereof are used to mount the filter device 1 to the ventilating means 2 and/or the holder for this ventilating means 2. The connection between the holding element 9 and the ventilating means 2 or the mounting structure thereof may vary. According to a preferred embodiment shown in FIG. 13, lateral clamping devices 22 hold the holding elements 9 together onto a front face of the ventilating means 2, wherein the clamping device 22 may include fastening clamps 23 which engage with a locking contour of the ventilating means 2. In the embodiment of FIG. 13, the fastening clamps 23 have locking hooks at their tips which are in locking engagement with lateral protrusions of the ventilating means 2. The said fastening clamps 23 may be deflected elastically so as to disengage from the ventilating means 2. In another embodiment the holding element 9 may be adapted to be attached to a protective grating that may be necessary as protection against undesired touching or contacting ventilator blades 15 in particular in a rotating state.

Figure 14:
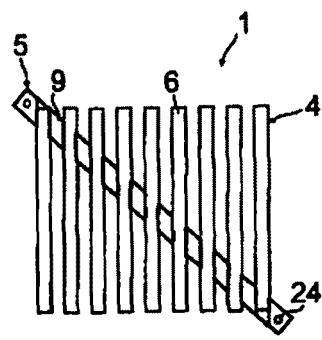
FIG. 14: a front view of a filter device according to a further embodiment of the present invention, wherein a beam-shaped holding element for holding the filter elements extends diagonally across the filter layer.
Figure 15:
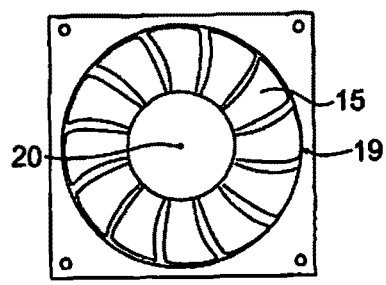
FIG. 15: a front view of a ventilating means similar to FIG. 11, FIG. 16: a front view of the filter device of FIG. 14 attached to the ventilating means of FIG. 15, FIG. 17: a filter device including spiral-shaped, snake-like filter rods held by a common holding element, wherein part A of FIG. 17 shows a front view of the spiral filter rods when viewed in the direction of the spiral axis, and part B of FIG. 17 shows a side view of the spiral filer rods when viewed perpendicular to the spiral axis to show that the two spiral filter rods are spaced apart from each other in the direction of the airflow and attached to the holding element with their inner ends.
Figure 16:
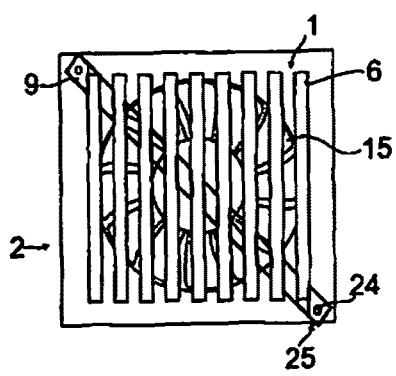

As shown in FIGS. 14-16, the bar-shaped holding element 9 does not necessarily extend across the filter layer 4 in a direction perpendicular to the longitudinal axis of the filter elements 9, but may extend diagonally. As shown in FIG. 14, the holding element 9 may extend at an angle of about 30° to 60° to the longitudinal axis of the filter elements 6, wherein the holding element 9 extends from a corner of the filter layer 4 to an opposite corner thereof, cf. FIG. 14.

As shown by FIG. 16, the connection of the holding element 9 to the ventilating means 2 does not necessarily include any clamping device 22, but may include a fastening device such as a screw or bolt connection. The ends of the holding element 9 extending beyond the circumference of the filter layer 4 may include through holes 24 through which screws or bolts may be connected to the ventilating means 2 or a holder thereof.

Figure 22:
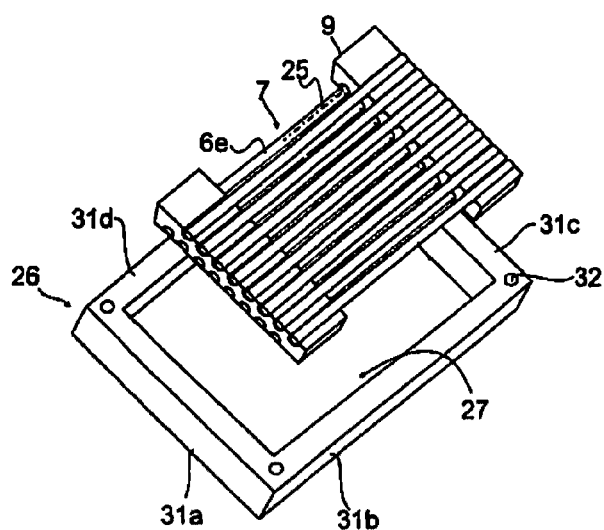
FIG. 22: a plain view of a filter layer similar to FIG. 8 which is inserted into the insertion recess of a mounting frame for indirectly mounting the filter layer in an air stream.

The filter layer 4 of the filter device 1 does not have to be mounted directly by means of the aforementioned holding element 9. As shown in FIG. 22, a mounting frame 26 may be used, which may have a closed ring shape as shown in FIG. 22, but also may have an open configuration for example by just having two or three of the four legs 31 of the mounting frame 26 of FIG. 22. The said mounting frame 26 is provided for indirect mounting the filter layer 4 to any suitable support structure as, for example, the aforementioned drive unit of a ventilator.

As shown in FIG. 22, the mounting frame 26 includes an insertion recess 27 which fully overlaps the projected area 28 of the filter layer 4 when viewed in the direction of the airflow 3 and/or perpendicular to the plane defined by the filter layer 4. This enables the filter layer 4 to be inserted and removed into/from the mounting frame 26 in the direction of the airflow 3 and/or perpendicular to the plane defined by the filter layer 4.

Preferably, the size and/or the dimensions of the insertion recess 27 is adapted to the size and/or dimensions and/or shape of the filter layer 4 such that the filter layer 4 is held in the insertion recess 27 in a press fitting manner. In particular, the width of the insertion recess 27 corresponds to the length of the filter layer 4 in the direction of the longitudinal axis of the straight filter sticks. Consequently, the filter sticks may be used as pressure columns providing the necessary friction at the end phases of the filter sticks to ensure fixture of the filter layer 4 in the mounting frame 26. In the crosswise direction, that means perpendicular to the longitudinal axis 25 of the filter sticks, the insertion recess may be formed wider than the filter layer 4 so there is no pressure onto the filter sticks perpendicular to the longitudinal axis thereof.

Figure 17A:
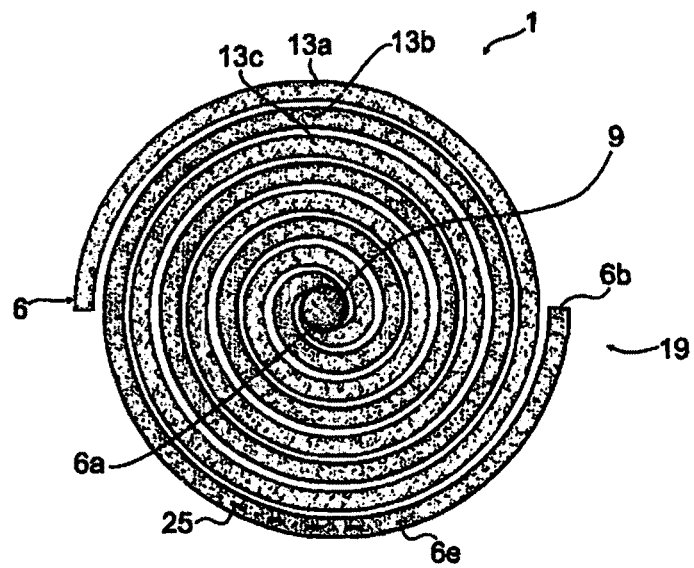
Figure 17B:
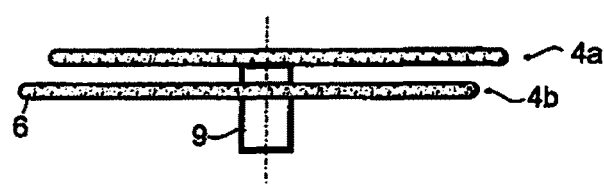

In the embodiment of FIG. 17, the filter device 1 includes filter elements 6 which are formed by spiral filter rods 13 and which are supported by a common holding element 9. More particularly, the inner ends 6a of the spiral-shaped filter elements 6 are rigidly connected to a rod-shaped holding element 9.

The spiral-shaped filter rods are offset relative to each other, wherein there is a rotational offset as well as an axial offset, cf. FIG. 17. The two spiral-shaped filter rods have basically identical shapes and are rotationally offset relative to each other by approximately 180° so that a first spiral filter rod overlaps the spacings between the legs of the second spiral filter rod when viewed in the direction of the spiral axis or the main direction of the airflow 3. Additionally, there is an axial offset in the direction of the said airflow 3. In other words, the inner ends 6a of the spiral-shaped filter elements 6 are attached to opposite sides of the circumference of the holding element 9 at different axial positions, cf. FIG. 17.

Such a central holding element 9 supporting the filter elements 6 in a cantilevered fashion maximizes the effective filter surface and minimizes the obstruction thereof by the filter holder 5. An advantageous way of mounting the filter device 1 of FIG. 17 to a ventilating means 2 is shown in FIG. 18. The central holding element may be used to mount the filter device 1 to the back side of a driving unit 16 of the ventilating means 2, wherein the holding element 9 may be connected to a holder for the said driving unit 16.

In another embodiment the spiral-shaped filter arrangement may be mounted by means of a mounting frame similar to that shown in FIG. 22. In this case the mounting frame may be formed circular or may comprise circular sections or segments and may include an insertion recess which fully overlaps the projected area of the filter layer 4 of the filter in FIG. 22 when viewed in the direction of the airflow and/or perpendicular to the plane defined by the filter layer 4.

In a further embodiment according to the invention, support elements may be provided between the filter layers 4a, 4b for supporting respectively stiffening the filter arrangement to achieve an improved rigidity. The support elements may be constructed as separate spacer respectively distance pieces or may be constructed as single piece together with one or more of the filter rods, whereby the support element(s) may protrude substantially perpendicular from the filter rod (i.e. in direction of the main air flow).

Figure 19:
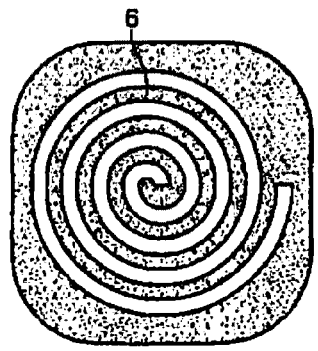
FIGS. 19 and 20: front views of two spiral filter rods having shapes complementary to each other, wherein each of the spiral filter rods has the shape of a linear spiral.
Figure 20:
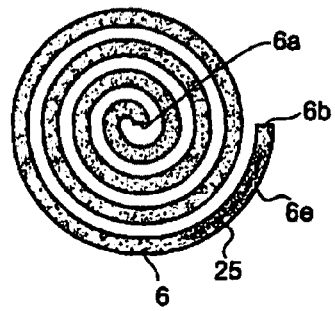

FIGS. 19 and 20 show another embodiment of spiral-shaped filter elements 6, wherein two spiral-shaped filter rods are shaped complementary to each other. As can be seen easily from a comparison of FIGS. 19 and 20, the spiral filter rod 6 of FIG. 20 exactly fits into the spacing 17 between the legs of the other spiral filter rod. In other words, if the two spiral filter rods are positioned in the same plane, a completely closed, void-free panel is defined. This complementary shape of the filter elements allows easy manufacturing thereof, for example by cutting such as laser cutting a plate-shaped blank.

The spiral filter rods of FIGS. 19 and 20 basically may be mounted as it is shown in FIGS. 17 and 18.

Figure 21A:
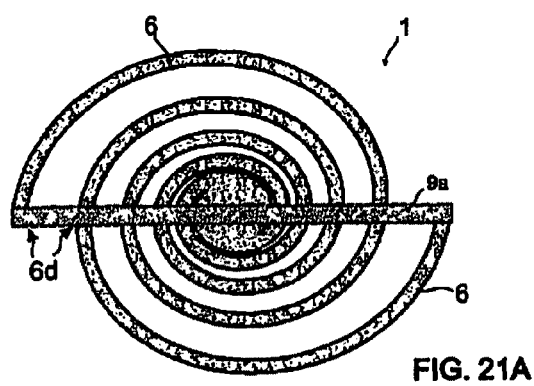
FIG. 21: a front view of two spiral rods integrally connected to a common centerpiece and having the space of a logarithmic spiral.
Figure 21B:
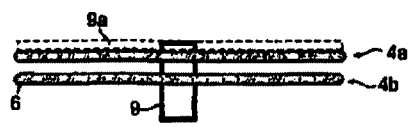

Contrary to FIGS. 17, 19 and 20 which show the filter rods to have the shape of a linear spiral, FIG. 21 shows two filter elements 6 having a shape of a logarithmic spiral. The filter rods forming the filter elements 6 are connected, with their inner ends 6a, to a common core section made of the same material as the filter rods so the spiral filter rods including the core section may be formed integrally in one piece from the same material. The said core section therefore may form the holding element 9 to hold the filter elements 6 in the airflow 3 of the ventilating means 2 as described for FIG. 18.

In a further embodiment the holding element 9 may comprise preferably bar- or beam-shaped sections 9a extending preferably diametral as shown in FIG. 21 for supporting respectively stiffening the filter arrangement to achieve an improved rigidity. The bar- or beam-shaped sections 9a may comprise a support surface 10 into which at least sections of the filter element 6 are embedded with the circumferential sides of their support section 6d.

As can be seen from FIG. 18, the unit comprising the ventilating means and the filter device may be mounted by means of a drive unit support that includes a mounting basis connected by means of a strut, an arm or any other support element connected to the driving unit 16.

Another preferred embodiment of the support structure for the units comprising the ventilating means 2 and the filter device 1 is shown in FIG. 23. The support device includes a substantially L-shaped support element 200 which includes a first leg 201 that extends substantially perpendicular to the air stream and the axis of rotation of the ventilating blades. Said first leg 201 may be formed a plate-shaped leg that includes a central recess that is slightly larger than the diameter of the circular area defined by the ventilator blades 15. Said first leg 201 is connected to a housing 300 of the unit which housing surrounds the driving unit 16 and preferably also the ventilator blades 15. As can be seen from FIG. 23, the said first leg 201 extends on the ventilator blade side of the drive unit 16, wherein said first leg 201 may extend in a plane close to the ventilator blades 15, preferably on the outer front face thereof.

The L-shaped support element further includes a second leg 202 rigidly connected to the first leg 201 and also may be substantially plate-shaped. Said second leg 202 extends from said first leg 201 along the lateral side of the ventilating means 2 substantially parallel to the air stream and the axis of rotation of the ventilating blades 15, wherein said second leg 202 is spaced apart from said housing 300 surrounding the driving unit 16. The second leg 202 includes mounting means such as holes for screws or other fixing means so that the support element may be mounted, for example, to the inner side of the cabinet of a gaming machine.

According to FIG. 23, the filter device 1 is positioned on the side of the driving unit 16 opposite to the ventilator blades 16. However, according to another embodiment, the filter device 1 may be positioned on the side of the ventilator blades 16 opposite to the driving unit 16 wherein the filter device 1 together with the first leg 201 of the support element 200 may be attached to the ventilation housing 300 at the opening orifice thereof.

When a filter device 1 with the filter sticks as described is used, the filter device may be positioned with either side facing the ventilation means. On the other hand, when a filter device 1 with a filter layer made of a spongy material as described is used, the filter device is positioned with the "right" side facing the ventilation means so the air flow goes through the filter layer in the right direction.

The invention claimed is:

1. Air cleaner for removing air-polluting materials trout an air stream, comprising a filter device (1) for separating the air-polluting materials from the air, said filter device including at least one filter layer (4) held by a lifter holder (5) in said airflow (3) substantially perpendicular to a main flow direction thereof, said filter layer (4) comprising a plurality of stick-shaped filter elements (6) neighboring each other, wherein said filter layer (4) has a periphery going along an outermost one of said filter elements (6e) and/or end portions of said filter elements (6), and at least one section (7, 8) of the periphery of said filter layer (4) is formed as an open side where the outermost filter element (6e) extends freely along the periphery of said filter layer (4), wherein said filter elements (6) define as filter layer plane and are formed by at least one curved, snake-shaped filter rod (13) having sections (13a, 13b, 13c) adjacent to and spaced from each other.

2. Air cleaner in accordance with claim 1, wherein said filter holder (5) extends along less than ⅔ of the periphery of said filter layer (4),
or only in a central section of said filter layer (4) leaving the entire periphery free, and said filter holder (5) includes a beam- or stick-shaped holding element (9) that extends transverse to the longitudinal axis of said filter elements (6) and extends parallel or perpendicular to the filter layer plane defined by said filter elements (6).

3. Air cleaner in accordance with claim 1, wherein said filter elements (6) are rigidly connected, to each other by said filter holder (5) to form a rigid, self-supporting structure projecting into said air stream from said filter holder (5).

4. Air cleaner in accordance with claim 1, wherein the filter elements (6) are held in said airflow (3) by said filter holder (5) in a cantilevered fashion with at least one end (6a) of the filter elements (6) extending free and unsupported, and said filter holder (5) is attached to a middle section (6c) of at least one of said filter elements (6) which thus has two free ends (6a, 6b), or said filter holder (5) is attached to an end section (6a) of at least one of said filter elements (5) which thus has one free end.

5. Air cleaner in accordance with claim 1, wherein said filter elements (6) are supported at their opposite ends only.

6. Air cleaner in accordance with claim 1, wherein said filter holder (5) includes a support surface (10) into which a support section (6d) of the filter elements (6) is embedded with a sector of ½π to 3/2π of the circumference of the supported section (6d) of the filter elements (6).

7. Air cleaner for removing air-polluting materials from an air stream, comprising a filter device (1) for separating the air-polluting materials from the air, said filter device including at least one filter layer (4) held by a filter holder (5) in said airflow (3) substantially perpendicular to a main flow direction thereof, said filter layer (4) comprising a plurality of stick-shaped filter elements (6) neighboring each other, wherein said filter layer (4) has a periphery going along an outermost one of said filter elements (6e) and/or end portions of said filter elements (6), and said filter holder (5) is formed integrally with said filter elements (6) in one piece of the same material, wherein said filter elements (6) define a filter layer plane and are formed by at least one curved, snake-shaped filter rod (13) having sections (13*a*, 13*b*, 13*c*) adjacent to and spaced from each other.

8. Air cleaner in accordance with claim 1, wherein said filter holder (5) includes a mounting surface (11) having hermaphrodite connecting means (12) for connecting at least two filter holders (S) to each other to create at least two filter layers (4) one above the other, and the filter elements (6) are positioned offset to said connecting means (12) such that the elements (6) in a first layer are positioned where a second layer shows spacings between its filter elements (6).

9. Air cleaner in accordance with claim 1, wherein said filter elements (6) are formed by at least two spiral filter rods (13) provided with a rotational offset such that, when viewed in the direction of the spiral axis, a first one of said spiral filter rods (13) overlaps the spacings (14) between the legs of the second one of said spiral rods (13).

10. Air cleaner in accordance with claim 9, wherein two spiral filter rods (13) identical or complementary to each other are positioned spaced from each other or one above the other, in substantially parallel planes spaced from each other in the direction of the airflow, and said two spiral filter rods are attached with their inner ends (6*a*) to the said filter holder (5), to different sections of said filter holder (5) spaced from each other in the direction of the airflow and/or to different circumferential section of said filter holder (5) rotationally offset from each other.

11. Air cleaner for removing air-polluting materials from an air stream, comprising a filter device (1) for separating the air-polluting materials from the air, said filter device including at least one filter layer (4) held by a filter holder (5) in said airflow (3) substantially perpendicular to a main flow direction thereof, said filter layer (4) comprising a plurality of stick-shaped filter elements (6) neighboring each other, wherein said filter layer (4) has a periphery going along an outermost one of said filter elements (6*e*) and/or end portions of said filter elements (6), and a mounting, frame (26) surrounding said filter layer (4) at a circumference thereof is provided with an insertion recess (27) fully overlapping a projected area (28) of the filter layer (4) when viewed in the direction of the airflow (3), thus enabling insertion and removal of the filter layer (4) into/from the mounting frame (26) in the direction of the airflow (3), wherein said filter elements (6) define a filter layer plane and are formed by at least one curved, snake-shaped filter rod (13) having sections (13*a*, 13*b*, 13*c*) adjacent to and spaced from each other.

12. Air cleaner in accordance with claim 11, wherein said insertion recess (27) is defined by a cylindrical through hole through said mounting frame (26), said through hole having an inner circumference basically corresponding to the outer circumference of the filter layer (4) and/or holding said filter layer in a press fit.

13. Air cleaner for removing air-polluting materials from an air stream, comprising a filter device (1) for separating, the air-polluting materials from the air, said filter device including at least one filter layer (4) held by a filter holder (5) in said air flow (3) substantially perpendicular to a main flow direction thereof said filter layer (4) comprising at least one filter element (6), the air cleaner further comprising ventilating means (2) for urging the airflow (3) through said filter device (1), said ventilating means including ventilator blades (15) driven by a driving unit (16), wherein the said filter device (1) is mounted to said driving unit (16) and/or a driving unit support by means of the said filter holder (5) at a side of the said driving unit (16) opposite to the said ventilator blades 15) or at a side of the ventilator blades (15) opposite to the driving unit (16), wherein said at least one filter element (6) defines a filter layer plane and is formed by at least one curved, snake-shaped filter rod (13) having sections (13*a*, 13*b*, 13*c*) adjacent to and spaced from each other.

14. Air cleaner in accordance with claim 13, wherein said driving unit support includes a L-shaped support element (200) having a first leg (201) that extends perpendicular to the air flow and is rigidly connected to the ventilating means (2), and a second leg (202) that is rigidly connected to said first leg (201) and extends parallel to the air flow along a peripheral side of said driving unit (16) and spaced apart from said driving unit (16), wherein said first leg (201) together with said filter device (1) is mounted to the opening orifice of a channel shaped ventilation housing surrounding the driving unit (16) and/or said ventilator blades (15).

15. Amusement and/or gaming machine for gambling, betting and/or entertaining, including a cabinet provided with at least one display means for displaying gaming information, a control panel for entering control commands, an electronic control unit for controlling the display means, said electronic control unit being provided inside said cabinet, and an air cleaner in accordance with claim 1 being provided inside said cabinet.

16. Air cleaner in accordance with claim 2, wherein said filter elements (6) are rigidly connected to each other by said filter holder (5) to form a rigid, self-supporting structure projecting into said air stream from said filter holder (5).

17. Air cleaner in accordance with claim 16, wherein the filter elements (6) are held in said airflow (3) by said filter holder (5) in a cantilevered fashion with at least one end (6*a*) of the filter elements (6) extending free and unsupported, and said filter holder (5) is attached to a middle section (6*c*) of at least one of said filter elements (6) which thus has two free ends (6*a*, 6*b*), or said filter holder (5) is attached to an end section (6*a*) of at least one of said filter elements (5) which thus has one free end.

18. Air cleaner in accordance with claim 3, wherein the filter elements (6) are held in said airflow (3) by said filter holder (5) in as cantilevered fashion with at least one end (6*a*) of the filter elements (6) extending free and unsupported, and said filter holder (5) is attached to a middle section (6*c*) of at least one of said filter elements (6) which thus has two free ends (6*a*, 6*b*), or said filter holder (5) is attached to an end section (6*a*) of at least one of said filter elements (5) which thus has one free end.

19. Air cleaner in accordance with claim 2, wherein the filter elements (6) are held in said airflow (3) by said filter holder (5) in as cantilevered fashion with at least one end (6*a*) of the filter elements (6) extending free and unsupported, and said filter holder (5) is attached to a middle section (6*c*) of at least one of said filter elements (6) which thus has two free ends (6*a*, 6*b*), or said filter holder (5) is attached to an end section (6*a*) of at least one of said filter elements (5) which thus has one free end.

* * * * *